United States Patent
Noe et al.

(10) Patent No.: US 7,319,161 B2
(45) Date of Patent: Jan. 15, 2008

(54) METHOD FOR PRODUCING CYCLOHEXANE DICARBOXYLIC ACIDS AND THE DERIVATIVES THEREOF

(75) Inventors: Ralf Noe, Mannheim (DE); Hartmut Hibst, Schriesheim (DE); Klaus Halbritter, Heidelberg (DE); Melanie Maas-Brunner, Mannheim (DE); Boris Breitscheidel, Limburgerhof (DE); Gerd Kaibel, Lampertheim (DE); Klemens Massonne, Bad Dürkheim (DE); Axel Salden, Stuttgart (DE); Klaus Ebel, Lampertheim (DE); Eike Johannes Bergner, Schriesheim (DE); Frank Haese, Lambsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 525 days.

(21) Appl. No.: 10/467,234

(22) PCT Filed: Feb. 15, 2002

(86) PCT No.: PCT/EP02/01661

§ 371 (c)(1),
(2), (4) Date: Aug. 6, 2003

(87) PCT Pub. No.: WO02/066412

PCT Pub. Date: Aug. 29, 2002

(65) Prior Publication Data

US 2004/0054220 A1    Mar. 18, 2004

(30) Foreign Application Priority Data

Feb. 16, 2001  (DE) ................. 101 07 366
Jun. 29, 2001  (DE) ................. 101 31 260
Dec. 12, 2001  (DE) ................. 101 61 010

(51) Int. Cl.
*C07C 69/74* (2006.01)
*C07C 61/00* (2006.01)
*C07C 59/00* (2006.01)

(52) U.S. Cl. ................. 560/127; 562/509; 562/887
(58) Field of Classification Search ............... 560/127, 560/128, 114; 562/504, 510, 887, 888, 891
See application file for complete search history.

(56) References Cited

U.S. PATENT DOCUMENTS 2,794,811 A * 6/1957 Winstrom .............. 549/240
3,308,086 A * 3/1967 Wartman ............... 524/145
2002/0019559 A1    2/2002 Brunner et al.

FOREIGN PATENT DOCUMENTS

| CA | 2374924 | | 12/2000 |
|----|---------|---|---------|
| DE | 2823165 | * | 11/1979 |
| EP | 603 825 | | 6/1994 |
| JP | 06032788 | * | 2/1994 |
| JP | 10212285 | * | 8/1998 |
| WO | 98/33787 | | 8/1998 |
| WO | 200078704 | * | 12/2000 |

OTHER PUBLICATIONS

Abst. FR 2397-131.
Abst. DE 28 23 165.
Abst. JP 200003492.
Abst. JP 7011074.
Abst. JP 5295025.
Abst. JP 7138205.
Abst. JP 6306252.
Kogyo Kagaku Zashi, 62, 1838-1841(1959).
Bailey et al., vol. 78 2806-2808, Am.Chem.Soc.
Kohler et al., vol. 60, 2142-2148,Am.Chem.Soc.
Tetrahedron, vol. 41, No. 7 1329-1346, 1985, Aitken et al.
Rice et al., Jrl. Am.Chem.Soc. 75,1953,4911-4915.
Ito et al., Helvetica Chimica Acta, vol. 77(1994) 2071-2110.
Tetrahedron Letters, vol. 38, 19, 1997, 3409-3412, Zoller et al.
Nazarov et al., 269-275, Sterochemistry of Cyclic compounds.
Fieser et al., Vo. 64, 802-809, A Synthesis of 4, 10- Ace-1,2-benzanthracene . . . .
Russell et al., Aliphatic Semidones. 1693-1698, Apr. 1971.
Abst. JP 7173342.

* cited by examiner

*Primary Examiner*—Karl Puttlitz
(74) *Attorney, Agent, or Firm*—Novak Druce & Quigg, LLP

(57) ABSTRACT

The invention relates to a process for preparing cyclohexanedicarboxylic acids or derivatives thereof, such as esters and/or anhydrides, encompassing the reaction of diene/maleic acid anhydride mixtures, in particular of butadiene/maleic acid anhydride mixtures or of mixtures of maleic acid anhydrides and C5-dienes to give alkyl-substituted or unsubstituted cyclohexenedicarboxylic acid anhydrides in the condensed phase, ester formation, and then hydrogenation to give the corresponding cyclohexanedicarboxylic acid derivative, and also to the use of the cyclohexanedicarboxylic acids or derivatives thereof prepared according to the invention as plasticizers for plastics.

7 Claims, No Drawings

METHOD FOR PRODUCING CYCLOHEXANE DICARBOXYLIC ACIDS AND THE DERIVATIVES THEREOF

The invention relates to a process for preparing cyclohexanedicarboxylic acids or derivatives thereof, such as esters and/or anhydrides, encompassing the reaction of diene/maleic acid anhydride mixtures, in particular of butadiene/maleic acid anhydride mixtures or of mixtures of maleic acid anhydride and at least one C5-diene to give alkyl-substituted or unsubstituted cyclohexanedicarboxylic acid anhydrides in the condensed phase.

The invention further relates to the alkyl-substituted or unsubstituted cyclohexanedicarboxylic acids or derivatives thereof, mixtures, comprising one or more thereof, made in accordance with the invention as well as the use of the reaction products prepared according to the invention, i.e. of the resultant alkyl-substituted or unsubstituted cyclohexanedicarboxylic acid compounds, in particular of the cyclohexanedicarboxylic esters, as plasticizers in plastics, in particular for polyvinyl chloride (PVC) and polyvinyl butyral (PVB).

Phthalates, e.g. dibutyl, dioctyl, or diisononyl phthalates have hitherto been used very frequently as plasticizers in plastics, such as PVC, as is apparent from FR-A 23 97 131. However, they have recently been alleged to be hazardous to health, and their use in plastics, for example in toy production, is subject to increasing criticism and has now been forbidden in some countries. Experiments on animals have now shown that phthalates can cause peroxisome proliferation, which is a cause of the liver tumors arising in long-term studies on mice and rats.

The use of some cyclohexane-1,2-dicarboxylic esters as plasticizers is likewise known from the prior art. For example, the use of dimethyl or diethyl cyclohexanedicarboxylates (DE-A 28 23 165) and di-2-ethylhexyl cyclohexane-1,2-dicarboxylate (DE-A 12 63 296) as plasticizers in plastics has been described.

PCT/EP 98/08346 discloses that cyclohexanepolycarboxylic acids and derivatives thereof can be used as plasticizers. In this connection it is disclosed that the density and viscosity of cyclohexanepolycarboxylic acids and derivatives thereof is lower than that of the phthalates mainly used as plasticizers hitherto, and moreover that these compounds lead, inter alia, to better low-temperature flexibility of the plastic when comparison is made with the use of the corresponding phthalates as plasticizers. PCT/EP 98/08346 also discloses that the dry-blend processing performance of cyclohexanepolycarboxylic acids and derivatives thereof is better than that of the corresponding phthalates and these compounds therefore have advantages in terms of increased production speed, and also in plastisol processing, via markedly lower viscosity.

EP-A 0 603 825 relates to a process for preparing cyclohexane-1,4-dicarboxylic acid by hydrogenating terephthalic acid with use of a supported palladium catalyst, the support used being aluminum oxide, silicon dioxide, or activated charcoal.

DE-A 199 77 977.2 discloses the use, as a plasticizer for plastics, of a cyclohexanepolycarboxylic acid or of a derivative thereof, where this brings about no biologically significant peroxisome proliferation, i.e. is regarded as toxicologically non-hazardous.

DE-A 199 27 978.0 relates to selected cyclohexane-1,3- and -1,4-dicarboxylic esters which are prepared by hydrogenation of the corresponding isophthalic and terephthalic esters, by way of contact with a hydrogen-containing gas in the presence of a catalyst having, as active metal, at least one metal of the 8th transition group of the periodic table of the elements, on its own or together with at least one metal of the 1st or 7th transition group of the periodic table of the elements, applied to a support. The use as plasticizer is likewise mentioned.

In principle, chosen diesters of norbornan-2,3-dicarboxylic acid, 4-methylcyclohexane-1,2-dicarboxylic acid and 3-methylcyclohexane-1,2-dicarboxylic acid are known, e.g. from JP 2000-034492, JP 70-11074, JP 71-73342, JP 52-95025 or JP 71-38205. Methylcyclohexane-1,2-dicarboxylic acid esters on basis of alcohols with 6 to 28 C atoms are until now only described as plasticizers for polyolefins, e.g. in JP 63-06252. Merely esters of norbornan-2,3-dicarboxylic acid with n-octanol or 2-ethylhexanol as alcohol component have been described for PVC (S. Matsuda, S. Kikkawa, Kogyo Kagaku Zasshi (1959) 62, 1838-1841).

The use of toxicologically non-hazardous plasticizers is particularly important for plastics used for producing articles for everyday use. Polyvinyl chloride, in particular, is used to produce many articles in daily use, including children's toys.

All of the processes utilized hitherto for preparing the cyclohexanecarboxylic acid derivatives are based on the hydrogenation of the underlying phthalic esters. This adds a stage to the reaction to prepare the plasticizers and makes the product more expensive.

It is an object of the present invention, therefore, in the first instance to provide a process which can prepare alkyl-substituted or unsubstituted cyclohexanedicarboxylic acids or derivatives thereof and which uses low-cost raw materials which are readily available in large quantities.

We have found that this object is achieved by means of a process for preparing an alkyl-substituted or unsubstituted cyclohexanedicarboxylic acid or a derivative thereof, encompassing the following sequences of steps (1) to (3):

(1) Converting a diene/maleic acid anhydride mixture to give alkyl-substituted or unsubstituted cyclohexenedicarboxylic acid anhydride in the condensed phase;

(2) Forming an ester from an alkyl-substituted or unsubstituted cyclohexenedicarboxylic acid anhydride;

(3) Hydrogenation of the alkyl-substituted or unsubstituted cyclohexene derivative of step (2) to give the corresponding derivative of cyclohexane;

or (1) Converting a diene/maleic acid anhydride mixture to give an alkyl-substituted or unsubstituted cyclohexenedicarboxylic acid anhydride in the condensed phase;

(3) Hydrogenation of the alkyl-substituted or unsubstituted cyclohexenedicarboxylic acid anhydride to give cyclohexanedicarboxylic anhydride;

(2) Forming an ester from the alkyl-substituted or unsubstituted cyclohexanedicarboxylic acid anhydride.

Therein and in the framework of the present invention, an alkyl-substituted cyclohexanedicarboxylic acid anhydride is a cyclohexane derivative with an alkyl substituent on the aliphatic ring or also a cyclohexane derivative, bridged with an alkyl residue, i.e. a bicyclical structure.

Within the framework of the present invention it is preferred if the cyclohexanedicarboxylic acid is unsubstituted or provided with a methyl substituent. In accordance with the invention, the methyl substituent may also be a methylene bridge.

Dienes are preferably dienes with less than 10 carbon atoms, in particular less than 6 carbon atoms, particularly preferably butadiene or dienes with 5 carbon atoms. Dienes appropriate in accordance with the invention are dienes with conjugated double bonds. Dienes with isolated double bonds do not react under the reaction conditions of the invention.

Thus, in a particularly preferred embodiment of the present invention, the invention relates to a process for preparing a cyclohexanedicarboxylic acid or a derivative thereof, encompassing the following sequences of steps (1) to (3):

(1) Converting a butadiene/maleic acid anhydride mixture to give cyclohexenedicarboxylic acid anhydride in the condensed phase;

(2) Forming an ester from a cyclohexenedicarboxylic acid anhydride;

(3) Hydrogenation of the cyclohexene derivative of step (2) to give the corresponding derivative of cyclohexane;

or (1) Converting a butadiene/maleic acid anhydride mixture to give cyclohexenedicarboxylic acid anhydride in the condensed phase;

(3) Hydrogenation of the cyclohexenedicarboxylic acid anhydride to give cyclohexanedicarboxylic acid anhydride;

(2) Forming an ester from the cyclohexanedicarboxylic acid anhydride.

The advantage of this process is the use of a crude maleic acid anhydride solution and a crude butadiene mixture for the reaction of step (1), where these comprise by-products and inert constituents, such as nitrogen, oxygen, or n- or isobutanes, and therefore the saving of one work-up step for obtaining pure butadiene and pure maleic anhydride.

In another preferred embodiment, the present invention relates to a process for preparing an alkyl-substituted cyclohexanedicarboxylic acid or a derivative thereof, comprising the following sequence of steps (1) to (3):

(1) Converting a mixture of maleic acid anhydride and at least one C5 diene to give an alkyl-substituted cyclohexenedicarboxylic acid anhydride in the condensed phase;

(2) Forming an ester from the alkyl-substituted cyclohexenedicarboxylic acid anhydride;

(3) Hydrogenation of the alkyl-substituted cyclohexene derivative of step (2) to give the corresponding derivative of cyclohexane;

or (1) Converting a mixture of maleic acid anhydride and at least one C5 diene to give an alkyl-substituted cyclohexenedicarboxylic acid anhydride in the condensed phase;

(3) Hydrogenation of the alkyl-substituted cyclohexenedicarboxylic acid anhydride to give cyclohexanedicarboxylic acid anhydride;

(2) Forming an ester from the alkyl-substituted cyclohexanedicarboxylic acid anhydride.

According to the present invention, "cyclohexanedicarboxylic acids and derivatives thereof" encompass the respective cyclohexanedicarboxylic acids themselves and also derivatives thereof, and particular mention should be made of mono- or diesters, and also anhydrides, of the cyclohexanedicarboxylic acids. The esters used are alkyl, cycloalkyl, and also alkoxyalkyl esters, where the alkyl, cycloalkyl, and alkoxyalkyl groups generally encompass from 1 to 30 carbon atoms, preferably from 2 to 20 carbon atoms, and particularly preferably from 3 to 18 carbon atoms, and may be branched or linear.

Suitable crude butadiene mixtures are butadiene-containing mixtures composed predominantly of hydrocarbons, the hydrocarbons other than butadiene being inert under the conditions of step (1) of the process.

Examples of these inert hydrocarbons are alkanes, monoalkenes, cycloalkanes, benzene, and dialkylbenzenes, for example propane, n-butane, 2-methylpropane, 1-butene, cis-2-butene, trans-2-butene, isobutene, cyclohexane, benzene, toluene and the xylenes.

There is generally no lower limit on the proportion of butadiene in this crude butadiene mixtures, but, for example for reasons of space-time yield in step (1) of the process, it is generally desirable for the butadiene content in these mixtures to be as high as possible. Another factor which can control the content of butadiene in the crude butadiene mixture is the intended makeup of the hydrocarbon stream remaining after stage (1) of the process: For example, if the intention is that the hydrocarbon stream be practically free from butadiene after the reaction of step (1) of the process, the content of butadiene in the mixture used should be adjusted correspondingly.

These crude butadiene mixtures preferably comprise from 20 to 95% by weight, in particular from 40 to 50% by weight, of butadiene.

A particularly low-cost crude butadiene mixture is what is known as the crude $C_4$ cut, whose butadiene content is generally from 40 to 50% by weight. This cut is produced industrially in large quantities (cf., for example, K. Weissermel, H.-J. Arpe, Industrielle Organische Chemie, VCH Weinheim, 5th edition, 1998, and also FR-A 1 343 169, DE-A 14 43 362 and DE-A 14 68 843). Using the crude $C_4$ cut it is possible to carry out step (1) of the process in such a way that the resultant hydrocarbon stream is practically butadiene-free. The makeup of this hydrocarbon stream is the same as that of what is known as raffinate I, which is normally obtained by other methods of butadiene extraction from the $C_4$ cut from crackers, and this stream can therefore be used as a replacement for raffinate I.

As is well known, the formation of azeotropes with other constituents of the $C_4$ cut generally makes it impossible to use distillation to separate butadiene from $C_4$ cuts, and complicated methods are therefore usually needed to extract the butadiene from these $C_4$ cuts.

Stage (1) of the process on its own therefore also provides a novel process for removing butadiene from butadiene-containing hydrocarbon mixtures, and in particular from $C_4$ cuts (cf. K. Weissermel, H.-J. Arpe, Industrielle Organische Chemie, VCH Weinheim, 5th edition, 1998).

Thus, method step (1) of the present invention is also a process for the separation of butadiene from butadiene-containing hydrocarbon flows, wherein the hydrocarbon flow is reacting with maleic acid anhydride and the resultant cyclohexene-dicarboxylic acid anhydride is separated from the remaining hydrocarbon flow.

In one preferred embodiment of the invention, the butadiene/maleic acid anhydride mixture for the reaction according to step (1) is obtained by a process comprising the oxidation of streams comprising n-butene or butadiene or a mixture thereof.

For the purposes of the present invention, the preferred butadiene used is 1,3-butadiene. In accordance with the invention, the butadiene/maleic acid anhydride mixture for the reaction according to step (1) may however also be obtained by a process comprising the oxidation of flows containing n-butane.

For the purposes of the present invention, streams comprising n-butene or butadiene or a mixture thereof are preferably a $C_4$ fraction of a raffinate stream. Examples of these are mixtures with the following makeup: butane from 10 to 90% by weight, butene from 10 to 90% by weight, where the butene fraction may have the following makeup: from 0 to 100% by weight, in particular from 0 to 80% by weight, particularly preferably from 0 to 50% by weight, of 1-butene, from 0 to 100% by weight, in particular from 0 to 80% by weight, particularly preferably from 0 to 50% by weight, of cis-2-butene, from 0 to 100% by weight, in particular from 0 to 80% by weight, particularly preferably from 0 to 50% by weight, of trans-2-butene, from 0 to 10% by weight of isobutene, and it is possible here that the stream also comprises small amounts, for example from 0 to 20% by weight, in particular from 0 to 10% by weight, of other hydrocarbons, in particular $C_5$ hydrocarbons. It is moreover also possible to use the pure n-butene or a mixture of a pure n-butene and butadiene.

A particularly preferred starting material used is that known as raffinate II, i.e. an n-butene-containing $C_4$ hydrocarbon mixture, as obtained from the $C_4$ cut of crackers after separating off most of the isobutene. However, removal of any butadiene also present is not an essential requirement of the process of the invention. There is therefore no need for a further purification step.

For the purposes of the present invention, use is in particular made of n-butene-rich streams which comprise at least 60% by weight, in particular at least 80% by weight, of n-butene and relatively small amounts of n- and isobutane and other hydrocarbons.

Substantial control of the oxidation of streams comprising n-butene or butadiene or a mixture therefore can be achieved by way of the use of various catalysts and the selection of the reaction conditions.

According to the invention, an example of the process used for obtaining the butadiene/maleic acid anhydride mixture for the reaction of step (1) comprises the oxidation of n-butene to give butadiene. According to the invention it is possible for this oxidation to be followed by addition of maleic acid anhydride (MA) to the crude butadiene in order to obtain a butadiene/maleic acid anhydride mixture for the reaction of step (1).

In one preferred embodiment, the present invention provides a process for preparing a cyclohexanedicarboxylic acid or a derivative thereof, which proceeds according to the following scheme (I):

Scheme (I)

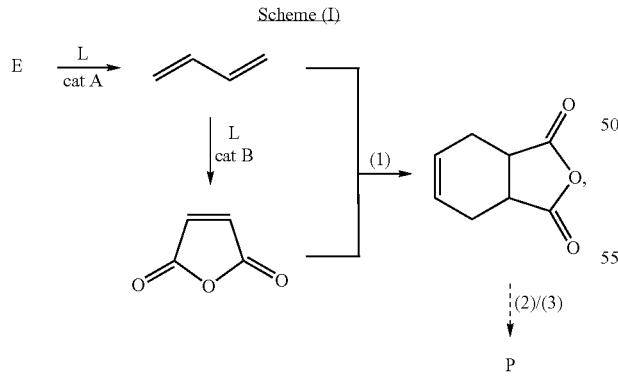

wherein in scheme (I) E is n-butenes (raffinate), L is air, cat A is catalyst system A, cat B is catalyst system B, and P is cyclohexane-1,2-dicarboxylic ester.

Steps (1) to (3) of the process of the invention are indicated in the reaction scheme here, and also within the reaction schemes which follow.

The reaction of butenes on a catalyst system A (cat A), for example a catalyst whose makeup is (Fe, Co)—Mo—O+ Bi—W—O, to give butadiene can be carried out with high butadiene yields of from 85 to 90%. U.S. Pat. No. 4,595,788 and U.S. Pat. No. 4,547,615 describe processes for preparing butadiene or conjugated diolefins. Butadiene is obtained in yields of more than 80% by using molybdenum-, bismuth-, or nickel-based catalysts in the reaction of C4 mixtures comprising n-butene. As has been shown by comparative experiments, these reactions also give small amounts of maleic acid anhydride (from 1 to 10%) alongside butadiene.

Since the butadiene is used for the reaction of step (1), MA content in the butadiene is not disruptive. It enables the dehydrogenation to obtain butadiene as raw material for the subsequent reaction to be operated in a particularly cost-effective manner with high butene conversion and incorporating an additional yield of MA, for example by the process of reaction scheme (III).

In one preferred embodiment of the invention, the n-butene to prepare the butadiene/maleic acid anhydride mixture is obtained by a process comprising the oxidation of flows containing n-butane.

It is also possible to start from linear butenes or butene-containing starting materials to obtain mixtures of butadiene and MA in suitable ratios of mixing.

The invention therefore also provides a process for preparing a cyclohexanedicarboxylic acid or a derivative thereof, where the butadiene/maleic acid anhydride mixture for the reaction according to step (1) is obtained by a process comprising the oxidation of n-butene to give a butadiene/maleic acid anhydride mixture.

In another preferred embodiment, the invention provides a process for preparing a cyclohexanedicarboxylic acid or a derivative thereof, which proceeds according to the following scheme (II):

Scheme (II)

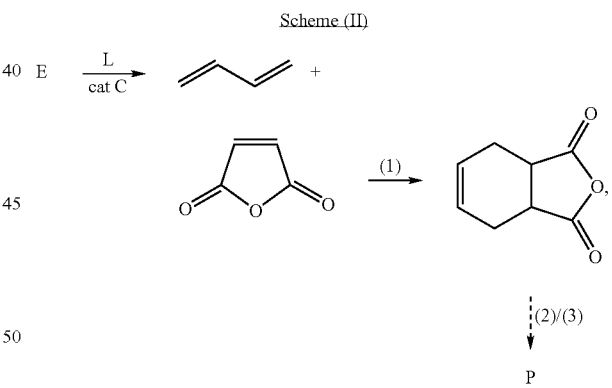

wherein in scheme (II) E is n-butenes (raffinate), L is air, cat C is catalyst system C, and P is cyclohexane-1,2-dicarboxylic ester.

This catalyst system C (cat C) is a catalyst system suitable for catalyzing the reaction of n-butenes to give a butadiene/maleic acid anhydride mixture.

The crude mixture of MA and butadiene may then be reacted in step (1) in a high-boiling, inert solvent used as absorption medium for the MA.

Mixtures of maleic acid anhydride (MA) and the butadiene intermediate can be obtained under mild reaction conditions by oxidizing unsaturated n-C4 hydrocarbons on a variety of heterogeneous catalysts. Suitable balance of reaction conditions and catalyst permit the butadiene and MA to be obtained. An example of a description of suitable conditions and catalysts is found in K. Weissermel, H.-J. Arpe, "Industrielle Organische Chemie", 4th edition, 1994, VCH Weinheim.

The further reaction of butadiene to give maleic acid anhydride takes place on a second catalyst system B (cat B), for example $SbMo_{3.06}Ti_{0.6}Nb_{0.1}Sn_{0.8}O_x/TiO_2$. Any maleic acid anhydride present in the feed is not disruptive and continues to be present, without decomposition, in the product stream. High overall yields can therefore be obtained by using stages in which butene is reacted on a first catalyst system A to give butadiene and then reacted on a second catalyst system B, and the ratio of butadiene and MA in the product stream can therefore be adjusted.

By way of example, DE 28 13 424 describes suitable conditions for the oxidation of butadiene to give maleic anhydride, using catalysts comprising oxides of antimony and molybdenum.

MA is obtained in the form of a crude solution from the reactor effluent by absorption in a high-boiling inert solvent. The absorption temperature is preferably above 55° C. in order to avoid crystallization of MA (melting point 55° C.). There is hardly any absorption of lower-boiling components (butadiene, by-products, water of combustion, carbon dioxide), and these components can readily be recovered from the exhaust gas, for example by pressure-swing absorption/temperature-swing absorption (PSA/TSA).

In contrast to industrial processes for MA preparation from C4 hydrocarbons, this stream is not, however, used as feed to the gas-phase oxidation to increase MA yield. Instead, for the purposes of the present invention, the crude mixture of the low boilers, which predominantly comprises butadiene, and also comprises other olefins and butanes, is a suitable raw material for the reaction of step (1), which is a Diels-Alder reaction with the crude MA solution. The crude mixture can be reacted with MA in the inert solvent used for MA absorption. The Diels-Alder product obtained is cyclohexanedicarboxylic acid anhydride. Suitable conditions for carrying out the reaction of step (1) are given by way of example in "Organic Syntheses", Coll. Vol. IV, 1963, J. Wiley & Sons, New York.

Another embodiment of the process of the invention includes the oxidative dehydrogenation of an n-butene-containing mixture to give a stream essentially consisting of butadiene and some yield of MA by-product. Of the mixture, which comprises butadiene and a little MA, a substream is reacted in a second oxidation to give MA, the substream ratio being as desired for the reaction of step (1). That substream from the first reaction which has not been subjected to further reaction is reacted with the product stream from the second oxidation in the condensed phase in step (1) to give the cyclohexenedicarboxylic acid anhydride. The discharge from the first oxidation reaction may be passed in gaseous form into the second oxidation, where it is further oxidized. Following the second oxidation, MA is then obtained as a crude solution from the reaction effluent, by absorption in a high-boiling inert solvent. The substream which comprises the gaseous butadiene which comes from the first oxidation and has not been subjected to further reaction may then be introduced into the crude solution of MA in the high-boiling solvent. The reaction of step (1) may be carried out directly with the resultant mixture of the crude products.

In particular, another embodiment of the invention provides a process for preparing a cyclohexanedicarboxylic acid or a derivative thereof, which proceeds by the following scheme (III):

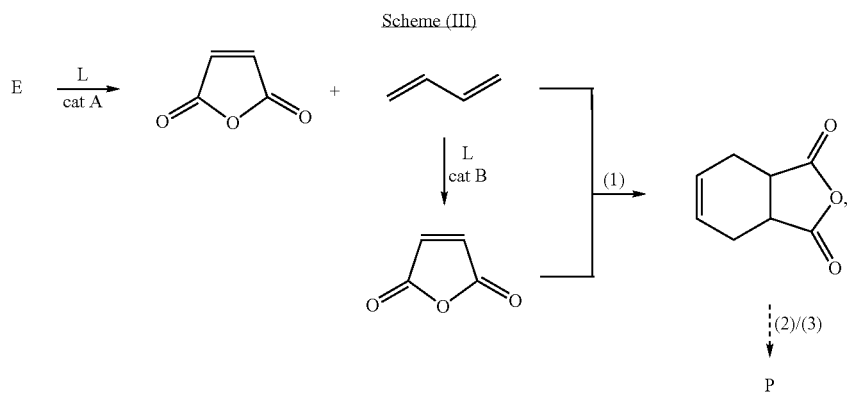

Scheme (III)

wherein in scheme (III) E is n-butenes (raffinate), L is air, cat A is catalyst system A, cat B is catalyst system B, and P is cyclohexane-1,2-dicarboxylic ester.

In another embodiment of the present invention, the butadiene/maleic acid anhydride mixture is subjected to a treatment prior to the reaction of step (1). An example of a treatment for the purposes of the present invention is the removal of a by-product, or in particular enrichment with one component in order to obtain a stoichiometric ratio of the components suitable for the reaction of step (1).

According to the invention, however, it is equally possible for the butadiene/maleic acid anhydride mixture not to be subjected to any treatment prior to the reaction of step (1).

According to the invention, it is also possible for the butadiene/maleic acid anhydride mixture for the reaction of step (1) to be obtained from crude butadiene and crude maleic anhydride. For the purposes of the present invention, crude butadiene and crude maleic acid anhydride are preferably streams which comprise at least 60% by weight, in particular at least 80% by weight, of butadiene and, respectively, maleic anhydride.

The in-situ preparation of butadiene and direct reaction in step (1) according to the invention can avoid the complicated use of controlled-release depot compounds which release the dienes in the homogeneous reaction medium used for the reaction, for example as described in DE 1 082 908, which describes a case where the use of depot compounds is needed to avoid using the pure form of dienes which readily polymerize.

Within the framework of the present invention, dienes besides butadienes may be C5 dienes, i.e. dienes with 5 C atoms. Besides the pure C5 dienes, mixtures of various dienes may also be used. In accordance with the invention, e.g. a C5 cut is inserted into the Diels-Alder reaction as per step (1). The C5 cut is a mixture of various C5 hydrocarbons, e.g. resulting from the cracking of hydrocarbons with longer chains. The advantage of the use of the C5 cut is that a time-consuming and expensive purification of the individual C5 dienes is avoided. Thus, the present invention relates also in a preferred embodiment to a process for the production of an alkyl-substituted cyclohexanedicarboxylic acid or a derivative thereof, wherein C5 cuts from a crack processes are used as C5 dienes.

In the Diels-Alder reaction with maleic acid anhydride (MA) as per step (1), merely the dienes cyclopentadiene, isoprene, and piperylene, i.e. the conjugated dienes are those C5 hydrocarbons of the C5 cut which react. E.g. in the C5 cut of crackers, 5 to 30% by weight, preferably 10 to 25% by weight, in particular 15 to 20% by weight of cyclopentadiene are contained, which can partially be present in the form of dicyclopentadiene, preferably 17% by weight, 5 to 25% by weight preferably 10 to 20% by weight, in particular 12 to 18% by weight isoprene, preferably 15% by weight and approximately 5 to 25% by weight, preferably 10 to 20% by weight, in particular 8 to 12% by weight piperylene, preferably 10% by weight. Moreover, the C5 cut may comprise other compounds, inert under the reaction conditions of the invention. The C5 cut may e.g. comprise n-pentane, i-pentane, i-pentene, 2-pentene or methylbutene, the sum of all components resulting in 100% by weight.

The Diels-Alder reaction between the C5 cut and MA is in the framework of the present invention performed thermally at temperatures of 40 to 250° C. without pressure or under the reaction system's own pressure in presence of radical polymerization inhibitors. If the C5 cut contains dicyclopentadiene besides cyclopentadiene and this is also meant to react, a two-step method may be used in the Diels-Alder reaction in accordance with the invention. Therein, at first monomeric dienes are reacted at a low temperature, e.g. between 40 and 140° C. with MA. Subsequently, the temperature is increased to 150 to 250° C. in order to react dicyclopentadiene. In accordance with the invention, however, it is possible to perform the reaction discontinuously in a reactor by step-wise increase of the temperature. However, in the same way it is possible to perform the reaction continuously in a sequence of reactors or reactor segments, operated at different temperatures. Appropriate reactors for the Diels-Alder reaction are e.g. stirring reactors or tubular reactors.

In accordance with the invention, it is also possible to perform the reaction of the C5 cut with MA in accordance with step (1) in such a way that the cyclopentadiene present as dicyclopentadiene is not reacted. Therefor, the temperature is held at below 140° C. in the Diels-Alder reaction. Such a reaction process leads to the portion of 5-norbornene-2,3-dicarboxylic acid anhydride in the product mixture being reduced.

The C5 hydrocarbon atoms of the C5 cut which do not react with maleic acid anhydride, can be easily separated after the reaction of step (1), e.g. by means of distillation.

In the reaction of the C5 cut as per step (1), a mixture of various anhydrides is obtained. Mixtures of 5-norbornene-2,3-dicarboxylic acid anhydride (mixture of endo and exo compound), 4-methyl-4-cyclohexene-1,2-dicarboxylic acid anhydride and 3-methyl-4-cyclohexene-1,2-dicarboxylic acid anhydride are obtained. Therein e.g. 0 to 30% by weight, preferably 10 to 25% by weight, especially preferred 15 to 20% by weight 5-norbornene-2,3-dicarboxylic acid anhydride, preferably 17% by weight (mixture of endo and exo compound), 0 to 25% by weight, preferably 10 to 20% by weight, in particular 12 to 18% by weight 4-methyl-4-cyclohexene-1,2-dicarboxyic acid anhydride, preferably 15% by weight, and 0 to 25% by weight, preferably 10 to 20% by weight, in particular 8 to 12% by weight 3-methyl-4-cyclohexene-1,2-dicarboxylic acid anhydride, preferably 10% by weight are present in the mixture.

In accordance with the invention it is possible to subject a mixture of an alkyl-substituted cyclohexenedicarboxylic acid anhydride resulting from step (1) via the reaction of MA and at least one C5 diene to a treatment. Within the framework of the present invention, the mixtures obtained as per step (1) by reaction of MA and at least one C5 diene can thus be further reacted directly or be separated into the pure compounds e.g. by a distillative process. It is possible in accordance with the invention to perform the subsequent reactions with the pure compounds. It is also possible to further react the mixture obtained in the reaction as per step (1).

In the following, explanations regarding cyclohexene or cyclohexanedicarboxylic acid derivatives refer to the alkyl-substituted as well as unsubstituted dicarboxylic acid derivatives or to the mixtures obtained in step (1).

According to the invention, the cyclohexenedicarboxylic acid anhydride obtained in step (1) may then be purified or be reacted directly in the form of a crude solution.

For the purposes of the present invention, the resultant crude solution of cyclohexenedicarboxylic acid anhydride may be esterified in step (2) to give the cyclohexenedicarboxylic ester. The formation of the ester here may take place by esterification with an alcohol with an alkyl-, cycloalkyl- or alkoxyalkyl-residue or with a mixture of two or more thereof wherein the alkyl-, cycloalkyl-, as well as alkoxyalkyl-groups contain generally 1 to 30, preferably 2 to 20 and particularly preferably 3 to 18 carbon atoms and may be branched or linear. In particular, the reaction is performed with linear or branched, saturated alcohols having from 1 to 20 carbon atoms, or using a mixture of two alcohols of this type. The reaction is carried out in the manner known to a skilled worker, as described by way of example in Organikum, 18th edition, 1990, Deutscher Verlag der Wissenschaften, Berlin.

In accordance with the invention, the esterification may in particular be performed with linear and branched alcohols with 1 to 18 C atoms, preferably 4 to 13 C atoms, particularly preferably 8 to 10 C atoms. Alcohols may be methanol, ethanol, linear or branched propanols, linear or branched butanols, linear or branched pentanols, linear or branched hexanols, linear or branched heptanols, linear or branched octanols, linear or branched nonanols, linear or branched decanols, linear or branched undecanols, linear or branched dodecanols, linear or branched tridecanols, linear or branched tetradecanols, linear or branched pentadecanols, linear or branched hexadecanols, linear or branched heptadecanols, linear or branched octadecanols, as well as mixtures of these alcohols.

The alcohols may be e.g. oxoaclohols, hydroformulation products of C5 to C12 alkenes and hydroformulation products of dimer-, trimer- and oligomer-ethene, of dimer-, trimer- and oligomer-propene, of dimer-, trimer- and oligomer-n- or -i-butene, of dimer-, trimer- and oligomer-n- or -i-pentene and of dimer-, trimer- and oligomer-n- or -i-hexene.

Particularly useful are e.g. hexanol mixtures with the Chemical Abstracts Number (in the following CAS no.) 68526-79-4, heptanol mixtures with the CAS no. 51774-11-9, octanol mixtures with the CAS no. 68526-83-0, octanol mixtures with the CAS no. 91994-92-2, 2-ethyl-hexanol, nonanol mixtures with the CAS no. 68526-84-1, nonanol mixtures with the CAS no. 3452-97-9, nonanol mixtures with the CAS no. 27458-94-2, decanol mixtures with the CAS no. 93821-11-5, decanol mixtures with the CAS no. 25339-17-7, 2 propylheptanol undecanol mixtures with the CAS no. 90604-37-8, dodecanol mixtures with the CAS no. 90604-37-8, tridecanol mixtures with the CAS no. 27458-92-0 and tridecanol mixtures with the CAS no. 68526-86-3.

In an alternate embodiment of the invention, the formation of the ester in step (2) may take place by dimerizing dienes on the cyclohexenedicarboxylic acid anhydride itself. This gives esters having C8 side chains. This provides a useful means of utilizing the butadiene from the prior oxidation of raffinate for this part of the process too. FR 15 79 244 and JP 50-005737 describe suitable conditions for the reaction to build up the ester side chain by way of butadiene dimerization.

For the purposes of the invention, it is also possible that the formation of the ester in step (2) takes place by an addition reaction of dienes on the cyclohexanedicarboxylic acid anhydride itself, or on the corresponding carboxylic acid. This process permits in particular the preparation of esters having C4 side chains.

The hydrogenation of the cyclohexene ring in step (3) may advantageously take place here together with the hydrogenation of the unsaturated side chain, in a single step of the reaction. The corresponding cyclohexane dialkyl ester is then obtained as a product of the reaction.

The hydrogenation of step (3) preferably takes place in the presence of a catalyst, using a hydrogen-containing gas. Examples of suitable catalysts are platinum or palladium catalysts bound to porous support materials. Other conditions of the hydrogenation reaction of step (3) are given by way of example in Organikum, 18th edition, 1990, Deutscher Verlag der Wissenschaften, Berlin. For the hydrogenation of the invention, fixed-bed catalysts, suspension catalyst and homogeneous hydrogenation catalysts may be used, e.g. described in Houben-Weyl "Methods of organic chemistry", Volume 4/1c. The hydrogenation can be effected with normal pressure or increased pressure at temperatures from 20° C. to 250° C. depending on the catalyst.

Other hydrogenation catalysts also particularly suitable for the purposes of the invention are those mentioned in WO 99/32427 and DE-A 199 27 978.0.

For the purposes of another preferred embodiment of the invention, it is also possible, following step (1), to begin with hydrogenation of the cyclohexenedicarboxylic acid anhydride to give cyclohexanedicarboxylic acid anhydride in step (3). According to the invention, the formation of the ester in step (2) as described above then gives the cyclohexanedicarboxylic ester.

With the method of the invention it is possible on the one hand to produce pure compounds, on the other hand, mixtures of various alkyl-substituted cyclohexane dicarboxylic acids or derivatives thereof may be produced. In particular when using a mixture of more than one C5 dienes for the reaction of step (1) it is possible to produce the pure compounds by means of a separation step at an arbitrary location in the production process, e.g. by distillation. It is, however, also possible to perform the process without a separation step and thus to obtain mixtures of various alkyl-substituted cyclohexanedicarboxylic acids or derivatives thereof.

In particular it is possible with the method of the invention to produce norbornan-2,3-dicarboxylic acid, 4-methylcyclohexane-1,2-dicarboxylic acid and 3-methylcyclohexane-1,2-dicarboxylic acid or derivatives thereof as pure compounds, i.e. with a content of >90% by weight. In the same way, mixtures comprising 0 to 70% by weight, preferably 10 to 65% by weight, in particular 15 to 60% by weight, particularly preferably 20 to 55% by weight norbornan-2,3-dicarboxylic acid or a derivative thereof, 0 to 70% by weight, preferably 10 to 65% by weight, in particular 15 to 60% by weight, particularly preferably 20 to 55% by weight 4-methylcyclohexane-1,2-dicarboxylic acid or a derivative thereof and 0 to 70% by weight, preferably 10 to 65% by weight, in particular 15 to 60% by weight, particularly preferred 20 to 55% by weight 3-methylcyclohexane-1,2-dicarboxylic acid or derivatives thereof are produced with the method of the invention, wherein the sum of the individual elements of the mixture results in 100% by weight.

Therefore, the invention also relates to alkyl-substituted or unsubstituted cyclohexanedicarboxylic acids or derivatives thereof, obtainable by a process, comprising the following steps (1) to (3):
(1) Converting a diene/maleic acid anhydride mixture to give an alkyl-substituted or unsubstituted cyclohexenedicarboxylic acid anhydride in the condensed phase;
(2) Forming an ester from the alkyl-substituted or unsubstituted cyclohexenedicarboxylic acid anhydride;
(3) Hydrogenation of the alkyl-substituted or unsubstituted cyclohexene derivative of step (2) to give the corresponding cyclohexane derivative;

or (1) Converting a diene/maleic acid anhydride mixture to give an alkyl-substituted or unsubstituted cyclohexenedicarboxylic acid anhydride in the condensed phase;
(3) Hydrogenation of the alkyl-substituted or unsubstituted cyclohexenedicarboxylic acid anhydride to give cyclohexanedicarboxylic acid anhydride;
(2) Forming an ester from the alkyl-substituted or unsubstituted cyclohexanedicarboxylic acid anhydride.

In another embodiment, the invention relates to alkyl substituted or unsubstituted cyclohexane dicarboxylic acids or derivatives thereof, obtainable by a process, comprising the following steps (1) to (3):
(1) Converting a butadiene/maleic acid anhydride mixture to give a cyclohexenedicarboxylic acid anhydride in the condensed phase;
(2) Forming an ester from the cyclohexenedicarboxylic acid anhydride;
(3) Hydrogenation of the cyclohexene derivative of step (2) to give the corresponding cyclohexane derivative;

or (1) Converting a butadiene/maleic acid anhydride mixture to give a cyclohexenedicarboxylic acid anhydride in the condensed phase;
(3) Hydrogenation of the cyclohexenedicarboxylic acid anhydride to give cyclohexanedicarboxylic acid anhydride;
(2) Forming an ester from the cyclohexanedicarboxylic acid anhydride.

In another preferred embodiment, the invention relates to alkyl-substituted cyclohexanedicarboxylic acids or derivatives thereof, obtainable by a process, comprising the following steps (1) to (3):

(1) Converting a mixture of maleic acid anhydride and at least one C5 diene to give an alkyl-substituted cyclohexenedicarboxylic acid anhydride in the condensed phase;
(2) Forming an ester from an alkyl-substituted cyclohexenedicarboxylic acid anhydride;
(3) Hydrogenation of the alkyl-substituted cyclohexene derivative of step (2) to give the corresponding cyclohexane derivative;

or (1) Converting a mixture of maleic acid anhydride and at least one C5 diene to give an alkyl-substituted cyclohexenedicarboxylic acid anhydride in the condensed phase;
(3) Hydrogenation of the alkyl-substituted cyclohexenedicarboxylic acid anhydride to give cyclohexanedicarboxylic acid anhydride;
(2) Forming an ester from the alkyl-substituted cyclohexanedicarboxylic acid anhydride.

Moreover, the present invention also relates to mixtures, comprising at least one alkyl-substituted or unsubstituted cyclohexanedicarboxylic acid or a derivative thereof.

In particular, the invention relates to mixtures comprising at least norbornan-2,3-dicarboxylic acid, 4-methylcyclohexane-1,2-dicarboxylic acid and 3-methylcyclohexane-1,2-dicarboxylic acid or derivatives thereof. Such mixtures have e.g. particularly advantageous properties for the use as plasticizer.

Particularly appropriate are therein the isononyl esters or 2-ethylhexyl esters of the respective cyclohexane dicarboxylic acid, wherein the isononanol used for producing the ester has the CAS number 27458-94-2. Thus, the present invention relates in another embodiment to mixtures comprising 0 to 70% by weight norbornan-2,3-dicarboxylic acid-bis-(2-ethylhexyl)ester, 2 to 70% by weight 4-methylcyclohexane-1,2-dicarboxylic acid-bis-(2-ethylhexyl)ester and 2 to 70% by weight 3-methylcyclohexane-1,2-dicarboxylic acid-bis-(2-ethylhexyl)ester as well as mixtures comprising 0 to 70% by weight norbornan-2,3-dicarboxylic acid-bis-(isononyl)ester, 2 to 70% by weight 4-methylcyclohexane-1,2-dicarboxylic acid-bis-(isononyl)ester and 2 to 70% by weight 3-methylcyclohexane-1,2-dicarboxylic acid-bis-(isononyl)ester.

The invention further provides the use of an alkyl-substituted or unsubstituted cyclohexanedicarboxylic acid according to the invention or a derivative thereof or of a mixture comprising such cyclohexanedicarboxylic acid or a derivative thereof as plasticizers for plastics, in particular polyvinylchloride (PVC) or polyvinylbutyral (PVB).

The proportions of the cyclohexanedicarboxylic acids prepared according to the invention, or a derivative thereof, added to the plastics are from 1 to 80% by weight, preferably from 5 to 55% by weight, particularly preferably from 10 to 50% by weight and in particular from 15 to 45% by weight.

For the purposes of the present invention, a plasticizer is a substance whose addition reduces the hardness of the plastic.

The esters of the invention have a low density and viscosity. The low density leads to advantageous volume costs of the plastics produced with the inventive plasticizers. The low viscosity improves the processing behavior when producing dry blends and leads to lower initial plastisol viscosities when producing pastes.

Moreover, the plasticizers in accordance with the invention cause an improvement of the cold-elastic properties of the plastics made with these plasticizers and an increased thermostability. The characterization of the cold-elastic properties is effected preferably by means of the so-called coldness-breaking temperature. This is the temperature at which a plastic shows first optically visible damages in the cold when mechanically acted upon. The determination of the coldness-breaking temperature is effected in accordance with DIN 53372. The characterization of the thermal stability is effected e.g. with PVC by means of the co-called HCl remaining stability. This is the interval during which plasticized PVC shows no decomposition connected with HCl formation at a temperature of 200° C. The determination of the HCl remaining stability is effected in accordance with VDE standard 0472, §614.

The cyclohexanedicarboxylic acids prepared according to the invention, or a derivative thereof, may also be used as plasticizer for mixtures of various plastics, for example of polyvinyl chloride or polyvinyl butyral with other plastics selected from the group consisting of homo- and copolymers based on ethylene, propylene, butadiene, vinyl acetate, glycidyl acrylate, glycidyl methacrylate, or of acrylates or methacrylates having alcohol components of branched or unbranched C1-C10 alcohols, styrene, or acrylonitrile.

Examples of the uses of the plastics plasticized with the cyclohexanedicarboxylic acids prepared according to the invention, or with a derivative thereof, include cases for electrical devices, such as kitchen machines or computers, piping, chemical engineering, cables, wire sheathing, window profiles, interior fittings, vehicle construction, furniture construction, floor coverings, production of gaskets, films, composite films, films for laminated safety glass, in particular TROSIFOL grade PVB films from HT-Troplast, phonographic disks, synthetic leather, toys, packaging containers, adhesive tape films, clothing, coatings, and fibers for fabrics.

In the following the present invention is illustrated with some examples.

EXAMPLES

Example 1

Diels-Alder Reaction of a C5 Cut with Maleic Acid Anhydride

A mixture of 98 g maleic acid anhydride (1.0 mole) and 180 g C5 cut with a content of 17% by weight cyclopentadiene (present as a mixture of approximately 2% by weight cyclopentadiene and approximately 15% by weight dicyclopentadiene), approximately 15% by weight isoprene and approximately 10% by weight piperylene was heated with 1000 ppm phenothiacine as radical inhibitor in an autoclave for initially 3 hours up to 70° C. and then for 5 hours up to 180° C. Subsequently, the not reacted hydrocarbons were distilled at normal pressure, finally in a vacuum. A mixture of the following dicarboxylic acid anhydrides resulted: approximately 35% 5-norbornene-2,3-di-carboxylic acid anhydride (mixture of endo and exo compounds), approximately 39% 4-methyl-4-cyclohexene-1,2-dicarboxylic acid anhydride and approximately 26% 3-methyl-4-cyclohexen-1,2-dicarboxylic acid anhydride.

Example 2

Hydrogenation 110 g of the reaction mixture from example 1 were dissolved in 400 ml THF. Subsequently 300 mg palladium on activated carbon (10% Pd) were added and hydrogenated at room temperature at 100 bar hydrogen pressure. The catalyst was then filtered off and the solvent was distilled off in a rotation evaporator. 112 g of a mixture of approximately 35% 5-norbornan-2,3-dicarboxylic acid anhydride, approximately 39% 4-methyl-4-cyclohexane-1,2-dicarboxylic acid anhydride and approximately 26% 3-methyl-4-cyclohexane-1,2-dicarboxylic acid anhydride were obtained.

Example 3

Esterification 106 g of the reaction mixture from example 2 were cooked with 250 g 2-ethylhexanol and 0.16 g titanium tetrabutylat as catalyst on a water sedimentary until no water was formed any longer. Then, the catalyst was hydrolyzed with a soda solution (content 0.5%), the water phase was separated and the organic phase was again washed with water. Finally, the excessive ethylhexanol was distilled off, wherein the last remaining alcohol was removed by stripping with vapor. 166 g of a mixture of approximately 35% 5-norbornan-2,3-dicarboxylic acid-bis-(2-ethylhexyl)ester, approximately 39% 4-methyl-4-cyclohexane-1,2-dicarboxylic acid-bis-(2-ethylhexyl)ester and approximately 26% 3-methyl-4-cyclohexane-1,2-dicarboxylic acid-bis-(2-ethylhexyl)ester were obtained.

Examples 4 and 5

Analogously to example 3, the esterification was performed with isononanol and 2-propylheptanol. Corresponding ester mixtures were obtained.

We claim:

1. A process for preparing an alkyl-substituted or unsubstituted cyclohexane-1,2-dicarboxylic acid, or a mono- or diester or anhydride thereof, comprising the following sequences of steps (1) to (3):
   (1) Converting a diene/maleic acid anhydride mixture to give alkyl-substituted or unsubstituted cyclohexenedicarboxylic acid anhydride in the condensed phase;
   (2) Forming an ester from an alkyl-substituted or unsubstituted cyclohexenedicarboxylic acid anhydride;
   (3) Hydrogenation of the alkyl-substituted or unsubstituted cyclohexene ester of step (2) to give the corresponding ester of cyclohexane;
   or
   (1) Converting a diene/maleic acid anhydride mixture to give an alkyl-substituted or unsubstituted cyclohexenedicarboxylic acid anhydride in the condensed phase;
   (3) Hydrogenation of the alkyl-substituted or unsubstituted cyclohexenedicarboxylic acid anhydride to give cyclohexanedicarboxylic acid anhydride;
   (2) Forming an ester from the alkyl-substituted or unsubstituted cyclohexanedicarboxylic acid anhydride,
   and wherein the diene/maleic anhydride mixture for the reaction according to step (1) is a butadiene/maleic acid anhydride mixture which is obtained by a process comprising the oxidation of products containing n-butene or butadiene or a mixture thereof or by a process comprising the oxidation of n-butene to give butadiene or by a process comprising the oxidation of n-butene to give a butadiene/maleic acid anhydride mixture, or
   wherein the diene/maleic anhydride mixture for the reaction according to step (1) is a mixture of maleic acid anhydride and at least one C5 cut obtained in a crack process and comprising at least one C5 diene.

2. A process for preparing a cyclohexane-1,2-di-carboxylic acid, mono- or diesters or anhydrides thereof, as claimed in claim 1 comprising the following sequence of steps (1) to (3):
   (1) Converting a butadiene/maleic acid anhydride mixture to give cyclohexenedicarboxylic acid anhydride in the condensed phase;
   (2) Forming an ester from a cyclohexenedicarboxylic acid anhydride;
   (3) Hydrogenation of the cyclohexene ester of step (2) to give the corresponding ester of cyclohexane;
   or
   (1) Converting a butadiene/maleic acid anhydride mixture to give a cyclohexenedicarboxylic acid anhydride in the condensed phase;
   (3) Hydrogenation of the cyclohexenedicarboxylic acid anhydride to give cyclohexanedicarboxylic acid anhydride;
   (2) Forming an ester from the cyclohexanedicarboxylic acid anhydride,
   wherein the butadiene/maleic acid anhydride mixture for the reaction according to step (1) is obtained by a process comprising the oxidation of products containing n-butene or butadiene or a mixture thereof or by a process comprising the oxidation of n-butene to give butadiene or by a process comprising the oxidation of n-butene to give a butadiene/maleic acid anhydride mixture.

3. A process for preparing a cyclohexane-1,2-di-carboxylic acid, mono- or diesters or anhydrides thereof, as claimed in claim 2, wherein the n-butene to prepare the butadiene/maleic acid anhydride mixture for the reaction according to step (1) is obtained by a process comprising the oxidation of products comprising n-butane.

4. A process for preparing an alkyl-substituted cyclohexane-1,2dicarboxylic acid, mono- or diesters or anhydrides thereof, as claimed in claim 1, comprising the following sequences of steps (1) to (3):
   (1) Converting a mixture of maleic acid anhydride and at least one C5 diene to give alkyl-substituted cyclohexenedicarboxylic acid anhydride in the condensed phase;
   (2) Forming an ester from an alkyl-substituted cyclohexenedicarboxylic acid anhydride;
   (3) Hydrogenation of the alkyl-substituted cyclohexene ester of step (2) to give the corresponding ester of cyclohexane;
   or
   (1) Converting a mixture of maleic acid anhydride and at least one C5 diene to give an alkyl-substituted cyclohexenedicarboxylic acid anhydride in the condensed phase;
   (3) Hydrogenation of the alkyl-substituted cyclohexenedicarboxylic acid anhydride to give cyclohexanedicarboxylic acid anhydride;
   (2) Forming an ester from the alkyl-substituted cyclohexanedicarboxylic acid anhydride,
   wherein C5 cuts from a crack process are used as C5 diene.

5. A process for preparing a cyclohexane-1,2-di-carboxylic acid, mono- or diesters or anhydrides thereof, as claimed in claim 2, wherein the butadiene/maleic acid anhydride mixture for the reaction according to step (1) is obtained by a process comprising the oxidation of products containing n-butene or butadiene or a mixture thereof or by a process comprising the oxidation of n-butene to give butadiene or by a process comprising the oxidation of n-butene to give a butadiene/maleic acid anhydride mixture.

6. A process for preparing a cyclohexane-1,2-di-carboxylic acid, mono- or diesters or anhydrides thereof, as claimed in claim 5, wherein the n-butene to prepare the butadiene/maleic acid anhydride mixture for the reaction according to step (1) is obtained by a process comprising the oxidation of products comprising n-butane.

7. A mixture comprising at least one alkyl-substituted or unsubstituted cyclohexane-1,2-dicarboxylic acid or a mono- or diester or anhydride thereof, obtainable by a process comprising the following sequences of steps (1) to (3):
  (1) Converting a diene/maleic acid anhydride mixture to give alkyl-substituted or unsubstituted cyclohexenedicarboxylic acid anhydride in the condensed phase;
  (2) Forming an ester from an alkyl-substituted or unsubstituted cyclohexenedicarboxylic acid anhydride;
  (3) Hydrogenation of the alkyl-substituted or unsubstituted cyclohexene ester of step (2) to give the corresponding ester of cyclohexane;

or
  (1) Converting a diene/maleic acid anhydride mixture to give an alkyl-substituted or unsubstituted cyclohexene-dicarboxylic acid anhydride in the condensed phase;
  (3) Hydrogenation of the alkyl-substituted or unsubstituted cyclohexenedicarboxylic acid anhydride to give cyclohexanedicarboxylic acid anhydride;
  (2) Forming an ester from the alkyl-substituted or unsubstituted cyclohexanedicarboxylic acid anhydride, and wherein the diene/maleic anhydride mixture for the reaction according to step (1) is a butadiene/maleic acid anhydride mixture which is obtained by a process comprising the oxidation of products containing n-butene or butadiene or a mixture thereof or by a process comprising the oxidation of n-butene to give butadiene or by a process comprising the oxidation of n-butene to give a butadiene/maleic acid anhydride mixture, or wherein the diene/maleic anhydride mixture for the reaction according to step (1) is a mixture of maleic acid anhydride and at least one C5 cut obtained in a crack process and comprising at least one C5 diene, and which comprises at least norbornan-2,3-dicarboxylic acid, 4-methylcyclohexane-1,2-dicarboxylic acid and 3-methylcyclohexane-1,2dicarboxylic acid or a mono- or diester or anhydride of these dicarboxylic acids.

* * * * *

UNITED STATES PATENT AND TRADEMARK OFFICE
CERTIFICATE OF CORRECTION

PATENT NO. : 7,319,161 B2
APPLICATION NO. : 10/467234
DATED : January 15, 2008
INVENTOR(S) : Noe et al.

Page 1 of 1

It is certified that error appears in the above-identified patent and that said Letters Patent is hereby corrected as shown below:

In Claim 3, col. 16, indicated lines 36 and 37:
"cyclohexane-1,2-di-carboxylic acid" should read
--cyclohexane-1,2-dicarboxylic acid--

In Claim 4, col. 16, indicated lines 42 and 43:
"cyclohexane-1,2dicarboxylic acid" should read
--cyclohexane-1,2-dicarboxylic acid--

In Claim 5, col. 17, indicated lines 1 and 2:
"cyclohexane-1,2-di-carboxylic acid" should read
--cyclohexane-1,2-dicarboxylic acid--

In Claim 6, col. 17, indicated lines 10 and 11:
"cyclohexane-1,2-di-carboxylic acid" should read
--cyclohexane-1,2-dicarboxylic acid--

In Claim 7, col. 18, indicated lines 23 and 24:
"3-methylcyclohexane-1,2dicarboxylic acid" should read
--3-methylcyclohexane-1,2-dicarboxylic acid--

Signed and Sealed this

Twentieth Day of May, 2008

JON W. DUDAS
*Director of the United States Patent and Trademark Office*